United States Patent
Martinez et al.

(10) Patent No.: US 9,468,754 B2
(45) Date of Patent: Oct. 18, 2016

(54) LEADS FOR SELECTIVE SENSING AND VIRTUAL ELECTRODES

(75) Inventors: Gonzalo Martinez, Mendota Heights, MN (US); Timothy G. Laske, Shoreview, MN (US); Mark T. Marshall, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1876 days.

(21) Appl. No.: 12/474,645

(22) Filed: May 29, 2009

(65) Prior Publication Data

US 2010/0305675 A1 Dec. 2, 2010

(51) Int. Cl.
*A61N 1/05* (2006.01)

(52) U.S. Cl.
CPC .............. *A61N 1/056* (2013.01); *A61N 1/0534* (2013.01); *A61N 1/0563* (2013.01); *A61N 1/0541* (2013.01)

(58) Field of Classification Search
USPC .............................. 607/4, 5, 7, 119, 121–123
See application file for complete search history.

(56) References Cited

U.S. PATENT DOCUMENTS

| | | | |
|---|---|---|---|
| 4,336,811 A | 6/1982 | Beck et al. | |
| 4,760,852 A * | 8/1988 | Lekholm | 607/116 |
| 5,336,253 A | 8/1994 | Gordon et al. | |
| 5,342,414 A | 8/1994 | Mehra | |
| 5,531,782 A | 7/1996 | Kroll et al. | |
| 5,534,022 A * | 7/1996 | Hoffmann et al. | 607/119 |
| 5,654,030 A | 8/1997 | Munshi et al. | |
| 5,683,443 A * | 11/1997 | Munshi et al. | 607/119 |
| 5,833,714 A | 11/1998 | Loeb | |
| 5,849,031 A * | 12/1998 | Martinez et al. | 607/5 |
| 6,278,897 B1 | 8/2001 | Rutten et al. | |
| 6,327,498 B1 | 12/2001 | Kroll | |
| 7,236,828 B2 | 6/2007 | Casavant et al. | |
| 7,848,806 B1 * | 12/2010 | Kroll | 607/5 |
| 2004/0127966 A1 * | 7/2004 | Frericks et al. | 607/116 |
| 2005/0131509 A1 | 6/2005 | Atanassoska et al. | |
| 2005/0221671 A1 | 10/2005 | Lyu et al. | |
| 2006/0161206 A1 * | 7/2006 | Efimov et al. | 607/5 |
| 2007/0250142 A1 | 10/2007 | Francis et al. | |
| 2008/0004670 A1 * | 1/2008 | McVenes et al. | 607/36 |

OTHER PUBLICATIONS

Hideki Hayashi, MD et al., *Virtual Electrodes and the Induction of Fibrillation in Langendorff-Perfused Rabbit Ventricles: The Role of Intracellular Calcium*, Am J Physiol Heart Circ Physiol (Aug. 1, 2008), Title Page, pp. 2-20, Figures (7 pages).
PCT Notification of Transmittal of the International Search Report and the Written Opinion of the International Searching Authority.

\* cited by examiner

*Primary Examiner* — Eugene Wu

(57) ABSTRACT

Selective sensing implantable medical leads include pulsing and sensing portions and pulsing and not sensing portion. Leads and electrodes may be used in defibrillation and as integrated bipolar defibrillation electrodes. An entire electrode can pass charge while a valve metal or valve metal oxide portion of the electrode prevents the entire electrode from sensing, effectively rejecting unwanted signals. Differential conduction pathways, due to the valve metal and/or oxides thereof, cause the portions of the electrodes to conduct differently when used anodically and cathodically. Complex intracardiac electrical gradient can be formed along with a number of virtual electrodes within the tissue. Reentrant loops can thereby be pinned following defibrillation shock.

15 Claims, 6 Drawing Sheets

LEADS FOR SELECTIVE SENSING AND VIRTUAL ELECTRODES

INTRODUCTION

The present technology relates to leads and electrodes for sensing and pulsing, for example, implantable medical leads for coupling to an implantable medical device (IMD).

A wide variety of IMDs are used in the human body. IMDs can be manufactured as discrete units that may be selected by a physician for a particular clinical use and coupled at implantation with one or more medical electrical leads. IMDs may include an implantable pulse generator (IPG) or a physiologic monitor, and particular examples include cardiac pacemakers, cardioverter/defibrillators, cochlear implants, muscle and nerve stimulators, and deep brain stimulators. Such devices often include signal processing and/or pulse generating circuitry powered by a battery and enclosed within a hermetically sealed enclosure or housing, which may be referred to as a "can." The can is typically formed of a conductive and biocompatible metal, such as titanium, which is corrosion resistant when exposed to body fluids during chronic implant. A connector header attached to a mounting surface on the can enables coupling of the IMD with one or more leads, whereby electrical connection is made between lead electrodes and the circuitry enclosed within the housing.

Electrical leads typically support one or more stimulation and/or sensing electrodes and certain IMDs may employ all or part of the can as an electrode. The conductive surface of the can may operate in conjunction with one or more of the lead electrodes to deliver stimulation energy, sense electrical body signals, and/or sense impedance changes in tissue. For example, in the delivery of cardiac pacing pulses, the can may act as an anode or indifferent electrode in conjunction with a lead cathode, and for the delivery of monophasic or biphasic cardioversion/defibrillation shocks, the conductive surface of the can may act as a high voltage electrode in conjunction with at least one lead electrode of an opposite polarity.

Where the IMD operates as a defibrillator, for example, one or more electrical leads are coupled to a device that is implanted in a subcutaneous pocket, with the lead(s) extending therefrom via a transvenous route into a patient's heart in order to carry electrical pulses from the device. These electrical leads may be used for pacing, sensing, and/or defibrillation. For example, a lead may be implanted within the heart so that lead electrodes, coupled to conductors carried within a lead body, are positioned for proper sensing, efficient pacing, and defibrillation stimulation. A shadow area of the electrodes and the implanted position of each electrode are factors determining a threshold of shocking energy required to defibrillate the heart (defibrillation threshold-DFT). One commonly used shocking vector is formed between a right ventricular (RV) defibrillation electrode and a device implanted within a left pectoral region (RV-can); another further includes a third defibrillation electrode positioned within the superior vena cava (SVC), which is electrically common with the can of the device (RV-SVC+can).

Improved electrodes for sensing and pulsing are desirable. For example, defibrillation may result in side effects, including both contractile and electrical dysfunctions. Therefore, reduction in defibrillation energy is desirable. Electrodes that can reject unwanted signals would also prove more efficient and could provide a means to apply the most appropriate defibrillation shocks.

SUMMARY

The present technology includes systems, methods, articles of manufacture, and compositions that relate to implantable leads and electrodes. In some embodiments, the present disclosure provides an implantable medical lead that has an elongated lead body with a distal end and a proximal end, where the lead includes a first material capable of electrical pulsing and sensing and a second material capable of electrical pulsing and not sensing. The first material and second material may be coupled to comprise an electrode and there may be a plurality of such first and second materials. The plurality of first materials and the plurality of second materials may also be coupled to comprise a plurality of electrodes, wherein the electrodes may comprise at least one first material and at least one second material. The lead may further include one or more conventional electrodes.

In some embodiments, the present technology provides a method of selectively sensing and pulsing electrical signals using an implanted medical lead, the lead having an elongated lead body with a distal end, a proximal end, a first material capable of electrical pulsing and sensing, and a second material capable of electrical pulsing and not sensing. The method includes sensing an electrical signal using the first material and pulsing an electrical signal using the first material and second material. Sensing an electrical signal using the first material may include sensing an electrical signal indicative of cardiac arrhythmia, ventricular fibrillation, or ventricular tachycardia and pulsing may provide pacing or a defibrillation shock.

Some embodiments include a second implanted medical lead, the second lead having an elongated lead body with a distal end, a proximal end, a first material capable of electrical pulsing and sensing, and a second material capable of electrical pulsing and not sensing, wherein pulsing comprises pulsing an electrical signal using the first materials and second materials of the first lead and the second lead. Such pulsing may create at least one virtual electrode between the first and second leads. The first and second leads may be further positioned so that the at least one virtual electrode blocks a reentrant electrical signal.

DRAWINGS

The drawings described herein are for illustrative purposes only of selected embodiments and do not represent all possible implementations, and are not intended to limit the scope of the present disclosure.

FIG. 1 illustrates a part of an implantable medical lead constructed according to the present technology;

FIGS. 2A, 2B, and 2C illustrate differential conduction pathways and the formation of virtual electrodes during phased pulsing between two electrodes constructed according to the present technology, each electrode having regions capable of pulsing and sensing that alternate with regions capable of pulsing and not sensing;

DETAILED DESCRIPTION

Figure 1:
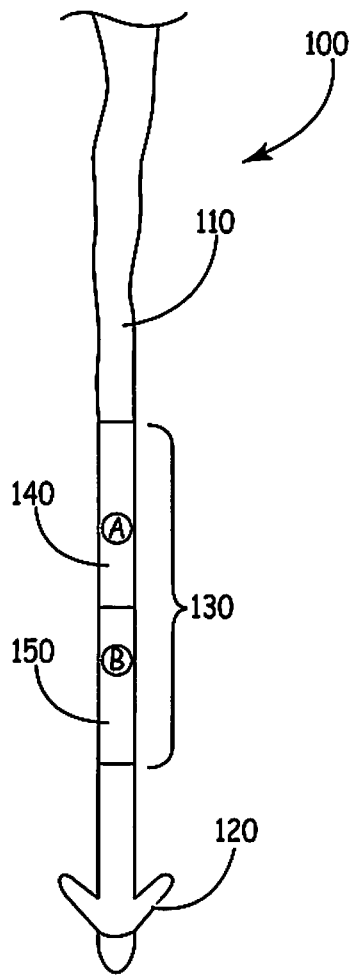

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

The present technology relates to electrical leads, such as pacing, sensing, and defibrillation leads, having electrodes operable to selectively sense and pulse. These leads may also be used to create virtual electrodes within tissue. An electrical lead may include at least one electrode where the electrode has at least two portions—one portion that passes an electrical pulse and is not used for sensing, and another portion that also passes an electrical pulse and is used for sensing. In this way, the electrode(s) on the electrical lead may be positioned for localized sensing while providing a broader pulsing area.

The present leads and electrodes may be constructed in several ways. In some embodiments, an electrical lead comprises first and second materials, where the first material can deliver charge in the positive and negative directions without restriction and can sense signals faster than the second material. The second material can also deliver charge, similar to the first material, but the second material may also either block signals below a certain voltage level, analogous to a Zener diode, or may attenuate the signals, analogous to an electronic filter or a series resistor, thereby allowing the first material to be the primary sensing source. The second material is also referred to herein as a selective sensing material.

In some embodiments, the electrode may be formed of a first material, which may be a conductive metal, where one or more portions are covered with the second material, which may be a selective sensing material such as a valve metal. The exposed portion(s) of the conductive metal can both sense and pulse while the valve metal coated portion(s) do not sense but can pulse. Alternatively, the electrode may be formed by coupling a conductive metal portion to a valve metal portion. For example, a platinum wire coil may be electrically coupled to a tantalum wire coil.

Alternative electrode constructions may include multi-conductor coils formed of co-wound insulated wires with different electrical properties. A selective sensing electrode may be formed by exposing one wire type, formed of the first material, in a certain region and another wire type, formed of the second material, in a different region. For example, the present technology may include and/or modify features of the electrodes and leads as described in U.S. Pat. No. 5,336,253 to Gordon et al.; U.S. Pat. No. 5,342,414 to Mehra; U.S. Pat. No. 6,327,498 to Kroll; U.S. Pat. No. 5,531,782 to Kroll et al.; and U.S. Pat. No. 7,108,549 to Lyu et al.

Examples of the first material include good conductor metals such as platinum, rhenium, vanadium, zirconium, palladium, iridium, titanium, niobium, tantalum, ruthenium, silver, molybdenum, silver chloride, cobalt, chromium, tungsten, magnesium, manganese, and their alloys. Examples of the first material also include nonmetals such as carbon, nitrides, conductive polymers, conductive ceramics and composites made of combinations of these materials, including combinations of metals and nonmetals.

Examples of the second material (used in their native oxide form or surface treated, i.e., anodized, doped, ion implanted, reactive sputtered, or any other chemical or physical treatment of the surface) include valve metals such as titanium, tungsten, chromium, aluminum, zirconium, hafnium, zinc, vanadium, niobium, tantalum, bismuth, antimony, and also include oxides, mixtures, and alloys thereof. Other materials that can be used to achieve selective sensing properties include metal oxides or mixtures of metal oxides, nitrides, carbides, semiconductors, conductive ceramics and ceramic oxides, conductive glasses, conductive polymers, gels, polymer-metal composites, and ceramic or glass composites. These various selective sensing materials may substitute for each other or may be used in combination as the second material. The second material may be further provided with an oxide coating (e.g., $Ta_2O_5$) which imparts useful properties such as corrosion resistance, EMI (electromagnetic interference) isolation and electrical resistance.

Additional examples of selective sensing materials include: tantalum pentoxide, titanium dioxide, niobium pentoxide, iridium oxide, p-type silicon, n-type silicon, zirconium oxide, doped germanium, gray tin, selenium, zinc oxide, zinc sulfide, tellurium, boron-carbon, boron-silicon, boron-phosphorus, carbon-silicon, silicon-germanium, silicon-tin, germanium-tin, doped diamond, doped zirconia, doped glasses, and organic rectifying materials such as polyacetylene, metal-phthalocyanine composites, poly(3,4-dicyanothiophene), and others. A specific example of how a material can be anodized to produce a rectifying material which can be used for selective sensing is described in the paper "Valve-metal type anodic oxide growth on iron disilicide ($FeSi_2$)", Journal of Materials Science Letters by Ashok K. Vijh, Guy Bélanger and R. Jacques of Institut de recherche d'Hydro-Québec, JOL 2PO Varennes, Quebec, Canada. In some embodiments, where the first material and second material comprise a similar or the same material, the second material may be anodized or treated to change its surface electrical properties. For example, where the first material comprises titanium the second material may comprise anodized titanium, which does not have as good of a conductive surface as the first material.

A defibrillation electrode, for example, may be fabricated with tantalum pentoxide ($Ta_2O_5$) and platinum/iridium (Pt/Ir), or similar metal couples, as an integrated bipolar defibrillation electrode. The entire electrode can be used to pass charge while only the portion containing the Pt/Ir can be used for sensing, thus effectively rejecting unwanted signals. Due the valve metal characteristics of the $Ta_2O_5$, the $Ta_2O_5$ portion(s) of the electrode conducts differently when used anodically and cathodically, which may further create an increase in the complexity of the intracardiac gradient and may be used to present one or more virtual electrodes within tissue. For example, an electrical lead may include one or more electrodes, where each electrode may include one or more materials capable of pulsing and sensing (e.g., Pt/Ir) and/or one or more materials capable of pulsing and not sensing (e.g., $Ta_2O_5$).

In some embodiments, electrodes and leads constructed according to the present technology can allow precise sensing and can also reduce defibrillation thresholds. For example, improved sensing is achieved by rejecting unwanted signals via proper placement of the sensing portion. This may be used to produce "true bipolar" functionality in an integrated bipolar lead design. The present design may also eliminate one circuit, using only two versus the three required in a conventional true bipolar defibrillation lead. What is more, spacing and patterns of $Ta_2O_5$ and Pt/Ir on the electrodes can reduce the defibrillation energy required to reach the DFT. These patterns may also be used to create complex electrical gradients and virtual electrodes within the tissue, reducing defibrillation energy and improving the pinning of reentrant circuits post-shock.

Virtual electrodes and how they relate to defibrillation are illustrated in Efimov et al., Virtual electrode hypothesis of defibrillation, Heart Rhythm, Vol. 3, No. 9 (September 2006) and Hayashi et al., Virtual Electrodes and the Induction of Fibrillation in Langendorff-Perfused Rabbit Ventricles: The Role of Intracellular Calcium, Am. J. Physiol. Heart Circ. Physiol. (Aug. 1, 2008), the relevant portions of which are incorporated herein by reference.

The terms "virtual electrode" and "activating function" are both used to refer to the driving force that drives transmembrane potential in either a depolarizing (positive) or hyperpolarizing (negative) direction after an externally applied electric field. A unipolar stimulus may produce both positive and negative polarization in a two-dimensional syncytium. These positive and negative polarizations are considered to be induced by virtual cathodes and virtual anodes, respectively. The virtual electrode theory predicts that an externally applied electric field can generate positive and negative virtual electrodes, which can depend on both the field configuration and tissue structure.

Basic mechanisms of ventricular tachycardia and fibrillation (VT/VF) can be addressed in the following ways: (1) defibrillation shock should terminate all or most wave fronts that sustain VT/VF; (2) the shock should not reinduce VT/VF; (3) the shock may need to suppress sources of VT/VF if they are focal in nature; and (4) the shock should not suppress postshock recovery of the normal sinus rhythm.

A strong electric shock applied during the refractory period can extend refractoriness. Thus, VT/VF wave fronts may be extinguished by either direct stimulation of excitable tissue or by extending the refractory period of depolarized tissue. In terms of virtual electrodes, these two phenomena are explained by the virtual cathode effect. With respect to the virtual anode, virtual anodes exist during defibrillation shocks and have effects on post-shock electrical activity. When applied to refractory myocardium, virtual anodes may de-excite cells and may either shorten the refractory period or fully restore excitability. When applied to excitable myocardium, virtual anodes hyperpolarize the tissue, but this hyper-polarization may be rapidly overwhelmed by depolarization produced by nearby virtual cathodes.

Shock-induced reentry may be induced by an adjacent virtual anode and virtual cathode. The anode de-excites tissue and restores excitability, while the cathode depolarizes tissue. When the two are within one space constant, a strong gradient of transmembrane potential is created, which may result in a post-shock wave front of break excitation. This wave front may propagate within the de-excited area of the virtual anode, and, if there is sufficient time for recovery of unaffected tissue and tissue subjected to virtual cathode-induced depolarization, this wave front may reenter and form arrhythmia circuit(s).

The defibrillation threshold may have a magnitude similar to the upper limit of vulnerability (ULV). Shocks larger than the ULV may induce stronger de-excitation, which accelerates conduction of the post-shock wave front of break excitation, leaving insufficient time for recovery of myocardium depolarized by virtual cathodes and rendering reentry essentially impossible.

Clinical implications of virtual electrodes in defibrillation include the following aspects. Anodal shocks may perform better compared to cathodal shocks, as applied from defibrillation leads. The virtual cathodes created adjacent to the real anode during anodal shocks can produce wave fronts that propagate inward, toward the area of de-excitation. These wave fronts can frequently collide and annihilate each other, whereas positive polarization under the real cathode during cathodal shocks can create wave fronts that propagate outward, having a greater propensity to return and create sustained reentry.

The efficacy of different waveforms also affects virtual electrodes and defibrillation. Biphasic shocks can have a lower defibrillation threshold than monophasic shocks. Monophasic shocks can be greater than the ULV to avoid the creation of a shock-induced phase singularity, which may reinduce reentry. On the other hand, the second phase of biphasic shocks can act to reverse the first-phase polarization, thus eliminating the substrate for postshock reentry. Monophasic ascending defibrillation waveforms may also be better than descending waveforms. Ascending waveforms produce maximum polarization at the end of the shock. Therefore, break excitation resulting from these shocks is likely to produce faster propagation into the de-excited regions and will not form reentry. However, descending waveforms tend to reach maximum polarization before the end of the shock and typically have a lower polarization at shock end, contributing to slower conduction and providing the substrate for shock-induced reentry.

Reentrant VT may be pinned or anchored at a functionally or anatomically heterogeneous region, which comprises the core of reentry. Virtual electrode polarization and the activating function suggest that areas near the core may experience greater polarization in response to an applied electric field compared with surrounding, and more homogeneous, tissue. Thus, the core of reentry can be preferentially excited with very small electric fields to destabilize and unpin reentrant VT from its stationary core. However, the external field should be applied at the right moment for the virtual electrode-induced excitation to properly interact with and terminate VT. For example, about a 20-fold reduction in defibrillation energy may be obtained with this unpinning method as compared with conventional defibrillation. This new low-energy approach may alleviate many of the side effects currently associated with strong electric shocks.

Referring now to FIG. 1, a bipolar design for a right ventricular lead 100 is shown. The lead 100 includes a body 110, constructed for example from insulating tubing, a connector (not shown) at a proximal end for coupling to an IMD, and a tip 120 at a distal end, which may include tissue attachment means, such as a screw, one or more barbs or anchor members, an adhesive, etc. The lead body 120 contains insulated conductors (not shown) which extend from the connector to an electrode 130. The electrode 130 may include a defibrillation coil formed of platinum or or a platinum alloy (e.g., Pt/Ir) having a Ta2O5 coating on a proximal portion 140 of the defibrillation coil, with the platinum exposed on a distal portion 150 of the lead.

The platinum distal portion 150 of the lead 100 is selectively placed to either mimic a bipolar sensing ring's size and location, or to produce precise sensing from another location along the length of the coil. For example, the platinum distal portion 150 may replace the ring electrode, as used in an RV lead constructed according to U.S. Pat. No. 7,236,828 to Casavant et al., or may be used in conjunction with such a ring electrode. Other configurations that may be adapted to include the present leads and electrodes include those illustrated in U.S. Pat. No. 5,336,253 to Gordon et al.; U.S. Pat. No. 5,342,414 to Mehra; U.S. Pat. No. 6,327,498 to Kroll; and U.S. Pat. No. 5,531,782 to Kroll et al.

During sensing, the platinum distal portion 150 can detect the local voltage thereby limiting the sensing to the platinum distal portion 150 of the electrode 130. The Ta2O5 coated proximal portion 140 filters out the sensed signal due to its high impedance, allowing the capturing of the evolved response by the platinum distal portion 150. During defibrillation shock, however, the Ta2O5 coating is overwhelmed by the delivered voltage and both the Ta2O5 coated proximal portion 140 and the platinum distal portion 150 conduct the current associated with the shock. The Ta2O5 coated proximal portion 140 may not conduct at pacing voltages.

In some embodiments, an electrode or a portion of an electrode, such as wire coil, may include Ta2O5 coated or anodized Ta wire. The Ta2O5 coated electrode or electrode portion may be used on the proximal end of an RV defibrillation coil to mitigate P-wave oversensing. The Ta2O5 electrode or electrode portion may also be used on the proximal end of an SVC coil to increase the distance between the active can electrode and the active sensing portion of the SVC coil for improved pseudo electrocardiogram (ECG) performance. P-wave oversensing and SVC coils are illustrated, for example, in U.S. Pat. No. 7,236,828 to Casavant et al.

In some embodiments, an electrical lead includes selective masking of additional defibrillation electrodes using a coating such as Ta2O5, and may include additional masking of the right ventricular coil. The platinum and Ta2O5 coated portions or an electrode may be alternated, resulting in striped or banded electrodes. Or, multiple electrodes may be used, where each electrode includes platinum and/or Ta2O5. When a defibrillation shock is delivered, typically in a biphasic form, these alternating regions result in differential conduction depending on the amplitude of the shock and its polarity. The result is the creation of complex gradients and virtual electrodes within the tissue that can reduce the defibrillation threshold (DFT) and increase pinning of reentrant circuits.

Figure 2A:
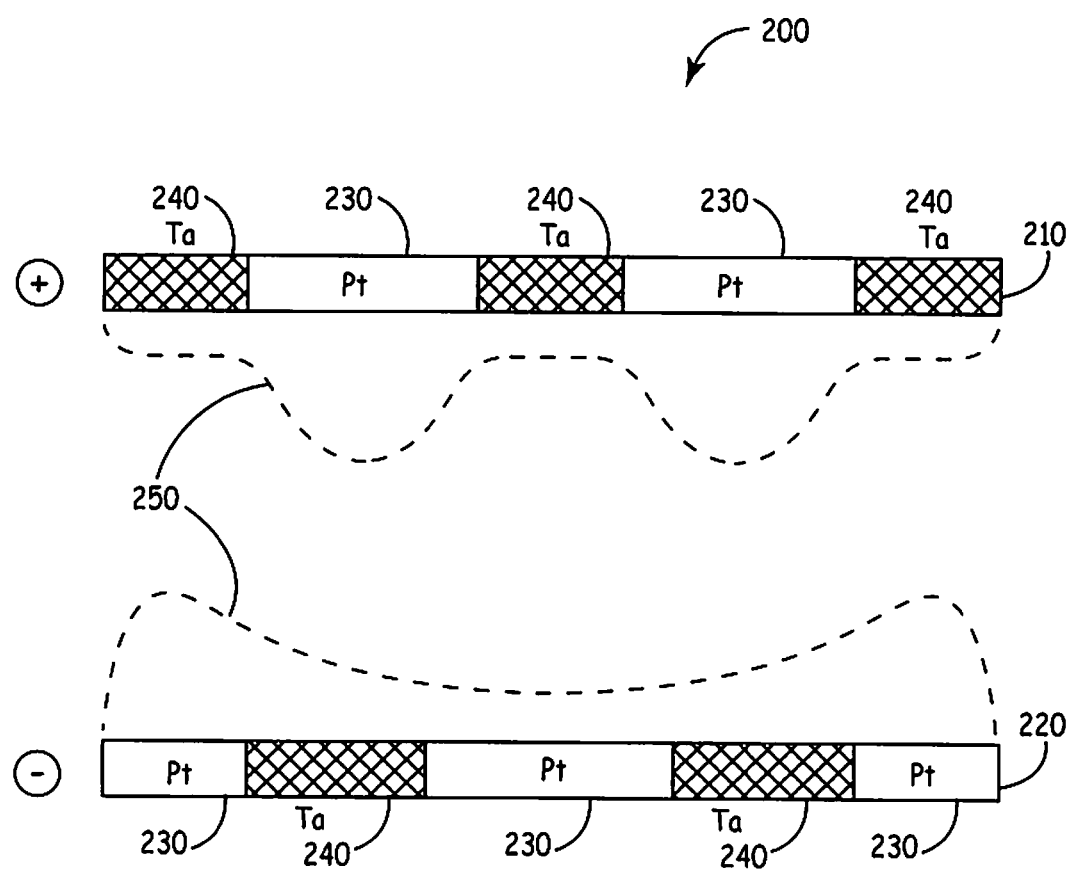

Referring now to FIG. 2A, a pair of electrodes 200 is shown where a first electrode 210 is operating as a cathode and a second electrode 220 is operating as an anode. Each of the first and second electrodes 210, 200 comprise platinum 230, or a platinum alloy, with alternating Ta2O5 coated portions 240. The alternating platinum 230 and Ta2O5 coated portions 240 result in differential conduction pathways, represented by lines 250, between the first and second electrodes 210, 220.

Figure 2B:
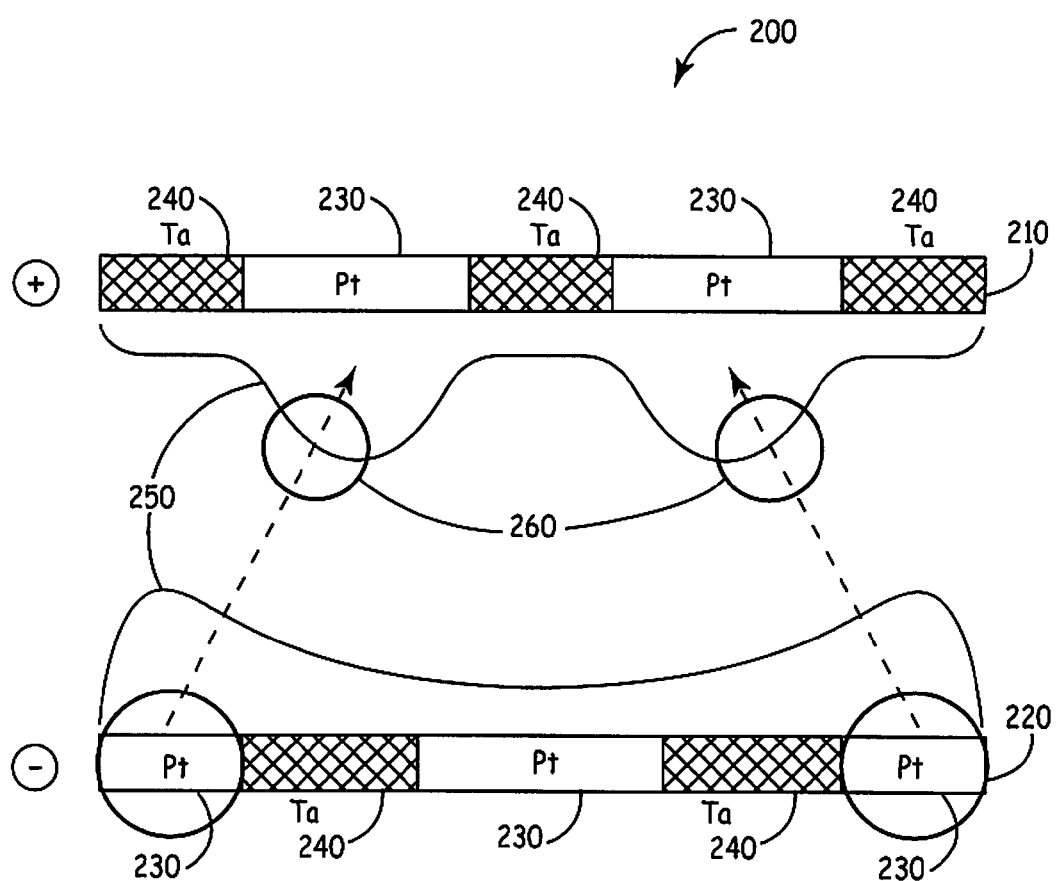

Referring now to FIG. 2B, a first phase of a biphasic defibrillation shock between the pair of electrodes 200 is shown. Conduction occurs between the first electrode 210, presently operating as a cathode, and the second electrode 220, presently operating as an anode 220. Following the differential conduction pathways 250, first virtual electrodes 260 are formed within the tissue between the first and second electrodes 210, 200.

Figure 2C:
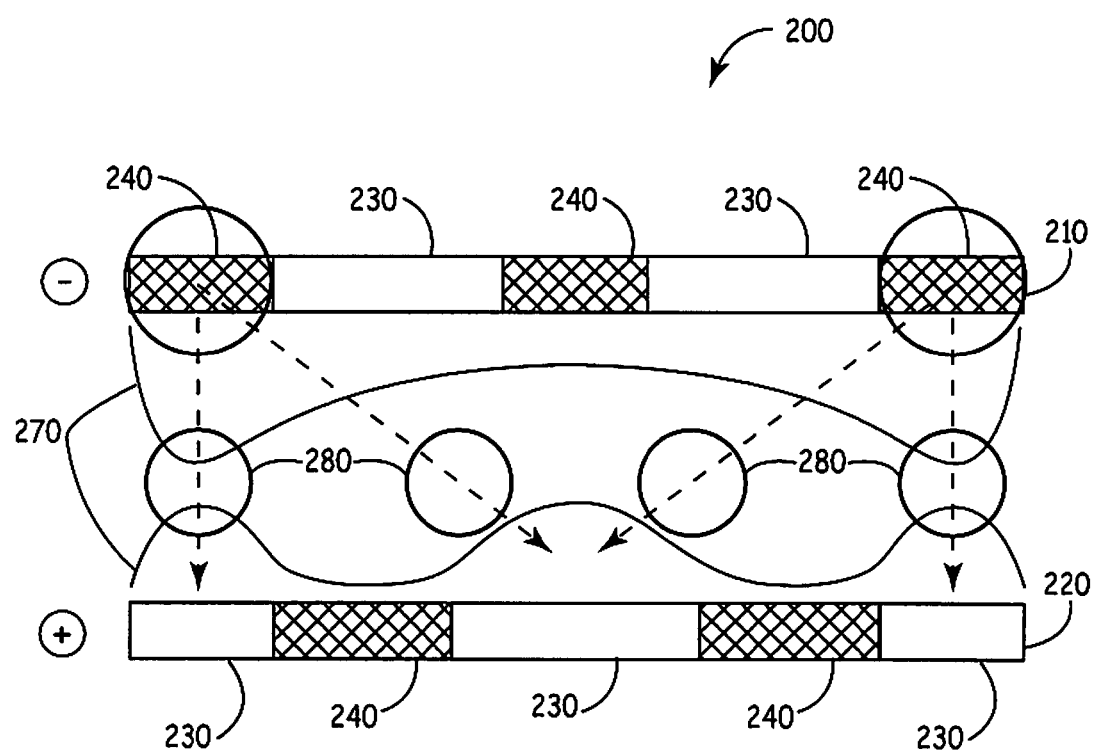

Referring now to FIG. 2C, a second phase of the biphasic defibrillation shock between the pair of electrodes 200 is shown. Polarity is flipped such that the first electrode 210 now operates as the anode and the second electrode 220 now operates as the cathode. Following reversed differential conduction pathways 270, second virtual electrodes 280 are formed between the first and second electrodes 210, 200. Biphasic defibrillation shock may therefore create a "wall" of depolarization between the pair of electrodes, illustrated by the sum of FIGS. 2B and 2C, which includes the first and second virtual electrodes 260, 280. This wall of depolarization may act as a barrier to stop reentrant loops.

Figure 3:
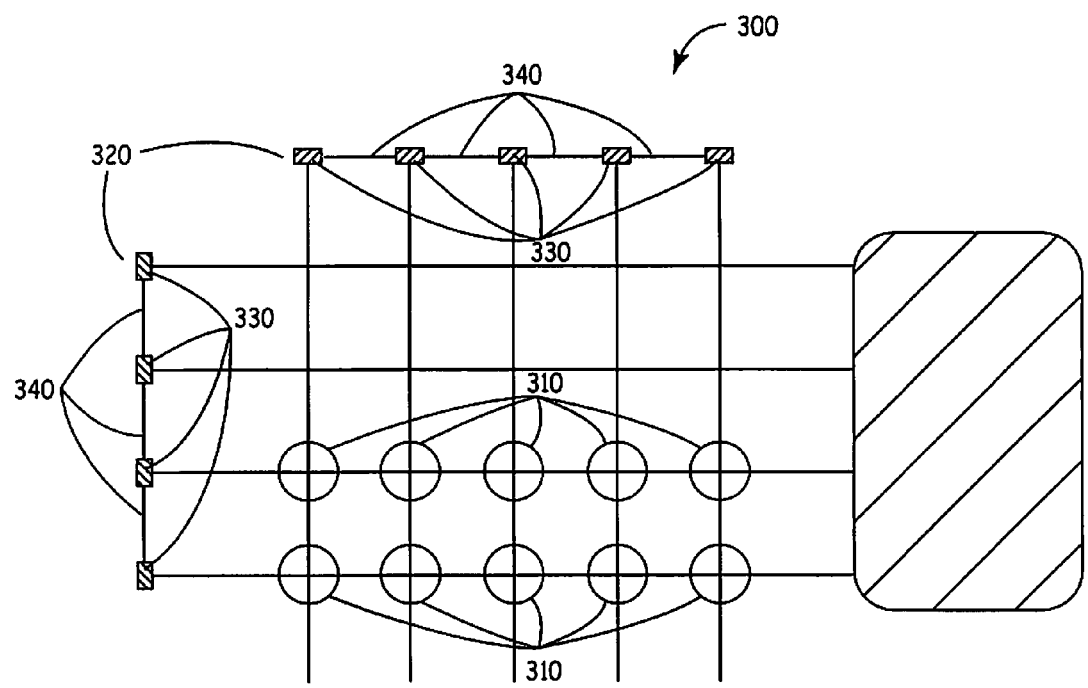
FIG. 3 illustrates a grid of virtual electrodes formed between two perpendicular electrodes constructed according to the present technology.

Referring now to FIG. 3, a grid 300 of virtual electrodes 310 formed within tissue is shown. The grid 300 results from two perpendicular electrodes 320 having alternating exposed platinum portions 330 (or platinum alloy) and Ta2O5 coated portions 340.

Figure 4:
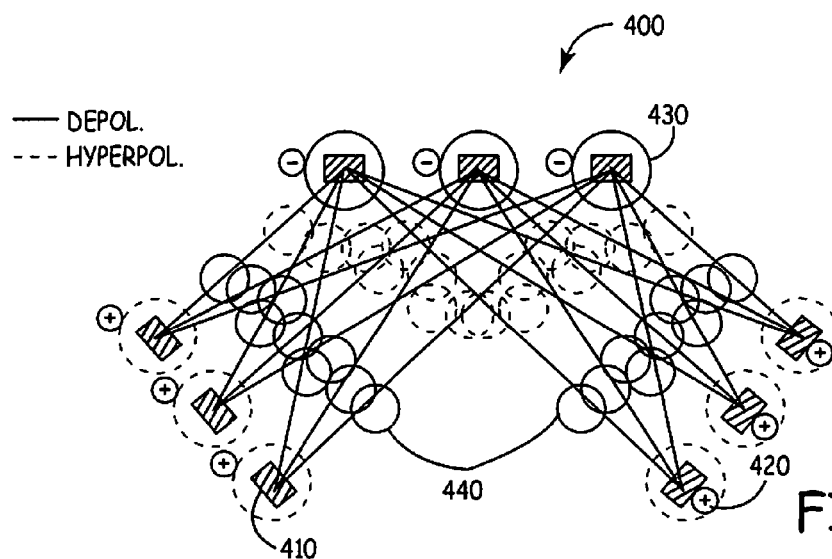
FIG. 4 illustrates three electrodes constructed according to the present technology that can form walls of virtual electrodes upon flipping polarity to block reentrant loops following defibrillation.

Referring now to FIG. 4, a system 400 including three electrodes is shown. The system 400 has first and second electrodes 410, 420 operating in concert and illustrated as cathodes, and a third electrode 430 illustrated as an anode.

Upon conduction of an electric pulse and subsequently flipping polarity, a "wall" of virtual electrodes 440 is formed within the tissue between each of the first and second electrodes 410, 420 and the third electrode 430. Thus, the first and second electrodes 410, 420 (optionally including additional electrodes, not shown) may be used to cordon off areas of tissue relative to the third electrode 430, operating as a barricade to inhibit reentrant loops through the virtual electrode wall in the tissue.

In some embodiments, the present technology includes an atrial synchronous ventricular inhibited (VDD) pacemaker ICD lead. The VDD ICD lead functions to sense cardiac activity in both the right atrium and ventricle combined with the ability to pace the cardiac rate from the ventricle. For example, this functionality is demonstrated by the Medtronic Model 5038 bipolar sensing (A & V) and bipolar pacing (V) lead. The VDD ICD lead, such as Model 14108 for DDD ICD leads, combines the sensing and pacing functions onto a single defibrillation electrode (e.g., single coil) ICD lead such as Medtronic models 6932, 6943, 6930, 6932, and 6935, and see those illustrated in U.S. Pat. No. 5,676,694 to Boser et al. The present technology improves these leads by including one or more electrodes capable of selective sensing and pacing.

Figure 5:
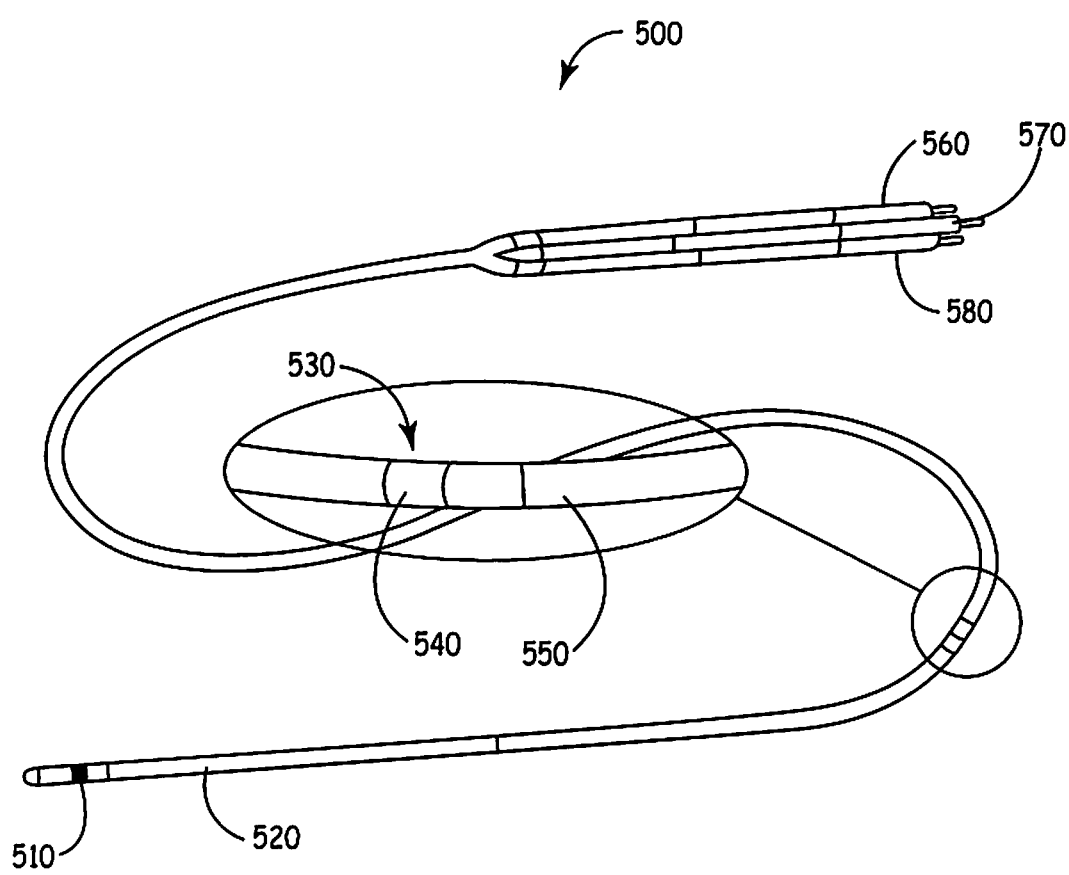
FIG. 5 illustrates an embodiment of an atrial synchronous ventricular inhibited pacemaker lead constructed according to the present technology.

Referring now to FIG. 5, an embodiment of a VDD pacemaker ICD lead 500 constructed according to the present technology is shown. A "pseudo-bipolar" electrode construction includes a region of Pt/Ir coil or ring electrode 510 and a length (e.g., 5-20 cm) of Ta wire coil electrode 520 with a Ta2O5 coating/layer. For example, the pseudo-bipolar electrode may be used in place of a proximal atrial electrode in a VDD pacemaker ICD lead. This provides the ability to maintain dual coil lead functionality that is used by the majority of electrophysiologists without sacrificing the specificity of atrial sensing, such as sensing that may be achieved with the Medtronic model 5038 or Model 14108 lead. The lead 500 also includes a proximal atrial electrode 530 having a Pt/Ir portion 540 and a Ta portion 550 with a Ta2O5 coating.

The VDD pacemaker ICD lead 500 may include four connections: (1) RV tip connector (e.g., low voltage unipolar IS-1 standard connector, ISO standard 5841-3); (2) connector for coated ventricular defibrillation coil with combined low voltage portion for sensing (e.g., Pt) and high voltage portion for defibrillation (Ta2O5), where the connector may be similar to those used for defibrillation leads with integrated bipolar sensing (e.g., DF-1 standard connector ISO standard 11318); (3) connector for an atrial pace/sense ring; and (4) connector for an atrial pace/sense ring or tip (as in Medtronic lead models 14107 and 14108); for example, (3) and (4) may be combined in a bipolar IS-1 connector.

Referring again to FIG. 5, a first connector 560 may include an RV tip connector. A second connector 570 may include a connector for the coated ventricular defibrillation coil with combined low voltage portion for sensing (i.e., Pt/Ir coil electrode 510) and high voltage portion for defibrillation (i.e., Ta wire coil electrode 520 with a Ta2O5 coating/layer). And a third connector 580 may include an atrial pace/sense ring or tip for the proximal atrial electrode 530 having a Pt/Ir portion 540 and a Ta portion 550 with a Ta2O5 coating.

The present leads can further improve on previous leads where the defibrillation coil is connected to both a low voltage connector (e.g., IS-1) and a high voltage connector (e.g., DF1), since the present leads allow use of a single connector, with connections to the sensing and defibrillator circuits made inside the ICD.

Connections (1) through (4) may also be realized by an IS-4 connector, as illustrated in U.S. Published Patent Application 2005/0221671A1 to Lyu et al., which comprises three low voltage connections and one high voltage connection. The present partially coated coil, allowing true bipolar ventricular sensing, makes the concept of a single pass dual chamber lead even more attractive. This configuration has the advantage of a single, high voltage coil which reduces leakage current and the risk of interference between high and low voltage signals via the connector sealings. The configuration also maintains the advantage of dual chamber sensing using a single lead, which may reduce inappropriate shocks and thromboembolic complications.

In some embodiments, a selective sensing and pulsing lead includes a partially coated ventricular defibrillation coil for true bipolar sensing and defibrillation and a configuration of atrial sensing electrodes as present in Medtronic model 5032/5038 VDD pacing leads or model 14108 DDD defibrillation lead. For example, the partially coated ventricular defibrillation coil may include a platinum wire coil electrode with a Ta2O5 coating/layer, as described herein. The atrial sensing electrodes may include a selective sensing portion, as well.

The present technology affords several benefits and advantages. The present systems and methods improve leads and electrodes by providing rectifying coatings to selectively sense with portions of an electrode coil, while pulsing with a larger contact area, and can further allow the creation of complex defibrillation fields, including virtual electrodes. The present electrodes and leads may reduce the chance of administering inappropriate defibrillation shocks. For example, one advantage of the present electrode and lead configurations is that single chamber pacing/defibrillation is combined with dual chamber sensing of atrial and ventricular signals. As a result, inappropriate detection of ventricular tachyarrhythmia may be reduced and consequently the administration of inappropriate shock may be reduced. The present electrode and lead configurations may also be implemented as single pass VDD or DDD defibrillation leads, depending on the ability of the atrial sense rings to provide reliable atrial pacing. The present electrodes also overcome limitations of integrated bipolar electrodes that use the entire coil for shocking and sensing. In addition, an implantable lead having one of the present electrodes, for example having a Ta2O5 portion and a Pt/Ir portion, can take the place of a lead having separate electrodes for pulsing and sensing in any IMD using such leads. The present leads and electrodes therefore reduce complexity and may reduce the number of conductors and connections required in lead manufacture.

Those of skill in the art will recognize that many of the embodiments and techniques provided by the present technology may be used, as applicable, in various implantable medical devices for treatment of various tissues. That is, the present teachings are not limited to cardiac applications and should be fairly construed to include leads and electrodes for other types of devices, such as deep brain stimulation leads, neurostimulation leads for pain and interstim applications, external sensing electrodes for EKG and ECG applications, etc. In addition, the embodiments and the examples described herein are exemplary and not intended to be limiting in describing the full scope of apparatus, systems, and methods of the present technology. Equivalent changes, modifications and variations of some embodiments, materials, compositions and methods can be made within the scope of the present technology, with substantially similar results.

What is claimed is:

1. A method of selectively sensing and pulsing electrical signals using an implanted medical lead, the lead having an elongated lead body with a distal end, a proximal end, a first material capable of electrical pulsing and sensing, and a second material capable of electrical pulsing and not sensing, the method comprising:
sensing an electrical signal using the first material;
pulsing an electrical signal using the first material and the second material.

2. The method of claim 1, wherein the second material comprises a valve metal.

3. The method of claim 2, wherein the valve metal is selected from the group consisting of titanium, tungsten, chromium, aluminum, zirconium, hafnium, zinc, vanadium, niobium, tantalum, bismuth, antimony, oxides thereof, alloys thereof, and combinations thereof.

4. The method of claim 1, wherein the first material comprises platinum or alloys thereof.

5. The method of claim 1, wherein pulsing an electrical signal using the first material and the second material comprises providing a defibrillation shock.

6. The method of claim 1, wherein the first material comprises a plurality of first portions, and sensing an electrical signal using the first portions comprises sensing an electrical signal from at least two of the first portions.

7. The method of claim 6, wherein one of the two first portions is located in an atrium and the other one of the first portions is located in a ventricle.

8. The method of claim 1, further comprising a second implanted medical lead, the second lead having an elongated lead body with a distal end, a proximal end, a first material capable of electrical pulsing and sensing, and a second material capable of electrical pulsing and not sensing, wherein pulsing comprises pulsing an electrical signal using the first materials and second materials of the first lead and the second lead.

9. The method of claim 8, wherein the pulsing comprises providing a defibrillation shock.

10. The method of claim 8, wherein the pulsing creates at least one virtual electrode between the first and second leads.

11. The method of claim 10, wherein the first and second leads are positioned so that the at least one virtual electrode blocks a reentrant electrical signal.

12. The method of claim 8, wherein the pulsing comprises providing a biphasic electrical signal.

13. The method of claim 1, wherein sensing an electrical signal using the first material comprises sensing an electrical signal indicative of cardiac arrhythmia, ventricular fibrillation, or ventricular tachycardia.

14. A method of selectively sensing and pulsing electrical signals using an implanted medical lead, the lead having an elongated lead body with a distal end, a proximal end, an electrode comprising a first external surface portion of a first material capable of electrical pulsing and sensing, and a second external surface portion of a second material capable of electrical pulsing and not sensing, the method comprising:
sensing an electrical signal using the first material;
pulsing an electrical signal using the first material and the second material.

15. A pacemaker lead having an elongated lead body with a distal end and a proximal end, the lead comprising:
a connector at the proximal end; and
a first electrode and a second electrode, the first electrode positioned closer to the distal end than the second electrode;
wherein the first electrode comprises a first external surface portion of a first material capable of electrical pulsing and sensing and a second external surface portion of a second material capable of electrical pulsing and not sensing.

* * * * *